US00PP31298P2

(12) United States Plant Patent
Hicks

(10) Patent No.: US PP31,298 P2
(45) Date of Patent: Dec. 31, 2019

(54) ***THUJA* PLANT NAMED 'NORTHERN SPIRE'**

(50) Latin Name: *Thuja plicata*
Varietal Denomination: Northern Spire

(71) Applicant: JRT Nurseries, Aldergrove (CA)

(72) Inventor: Jeff Hicks, Aldergrove (CA)

(73) Assignee: JRT NURSERIES, Aldergrove, BC (CA)

( * ) Notice: Subject to any disclaimer, the term of this patent is extended or adjusted under 35 U.S.C. 154(b) by 0 days.

(21) Appl. No.: 16/350,356

(22) Filed: Nov. 6, 2018

(51) Int. Cl.
*A01H 7/00* (2006.01)
*A01H 6/00* (2018.01)

(52) U.S. Cl.
USPC ..... Plt./213

(58) Field of Classification Search
USPC ..... Plt./213
CPC ... A01H 7/00; A01H 5/00; A01H 5/04; A01H 5/02; A01H 5/025
See application file for complete search history.

*Primary Examiner* — June Hwu
(74) *Attorney, Agent, or Firm* — Penny J. Aguirre

(57) ABSTRACT

A new cultivar of *Thuja plicata* named 'Northern Spire' that is characterized by its tightly branched growth habit, its uniform and narrow pyramidal plant habit that is ideal for hedging, its resistance to Keithia blight, its foliage that is dark green in spring and summer and turns russet red in fall and winter, and its deer resistance.

2 Drawing Sheets

Botanical classification:*Thuja plicata.*
Varietal denomination: 'Northern Spire'.

BACKGROUND OF THE INVENTION

The present invention relates to a new and distinct cultivar of *Thuja plicata* and will be referred to hereafter by its cultivar name, 'Northern Spire'. 'Northern Spire' represents a new cultivar of northern white cedar, an evergreen tree grown for landscape use and particularly useful for hedging.

The inventor discovered 'Northern Spire' as a naturally occurring branch mutation of 'Emerald Giant' (not patented) in 2001 that was growing in a production field in Pitt Meadows, British Columbia, Canada.

Asexual propagation of the new cultivar was first accomplished by the Inventor using stem cuttings in Pitt Meadows, British Columbia, Canada in the 2002. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Northern Spire' as a unique cultivar of *Thuja.*

1. 'Northern Spire' exhibits a tightly branched growth habit.
2. 'Northern Spire' exhibits a uniform and narrow pyramidal plant habit that is ideal for hedging.
3. 'Northern Spire' has shown resistance to Keithia blight.
4. 'Northern Spire' exhibits foliage that is dark green in spring and summer and turns russet red in fall and winter.
5. 'Northern Spire' exhibits deer resistance.

The parent plant of 'Northern Spire', 'Emerald Giant', differs from 'Northern Spire' in having a larger plant size (⅓ larger) and a wider pyramidal plant shape (65% less narrow). 'Northern Spire' can be most closely compared to the *Thuja plicata* cultivars 'De Rakt' (U.S. Plant Pat. No. 19,926) and 'Smaragd' (not patented). 'De Rakt' differs from from 'Northern Spire' in having a slower growth rate, finer textured foliage, in being less cold hardy, and in having green foliage in winter. 'Smaragd' differs from 'Northern Spire' in being less resistant to deer, less cold hardy, and less disease resistant, in shedding snow less readily, and in lacking russet fall foliage color.

BRIEF DESCRIPTION OF THE DRAWINGS

The accompanying colored photographs illustrate the overall appearance and distinct characteristics of the new *Thuja*. The photographs were taken of a four-year-old plant as grown outdoors in a 3-gallon container in Aldergrove, British Columbia, Washington.

Figure 1:
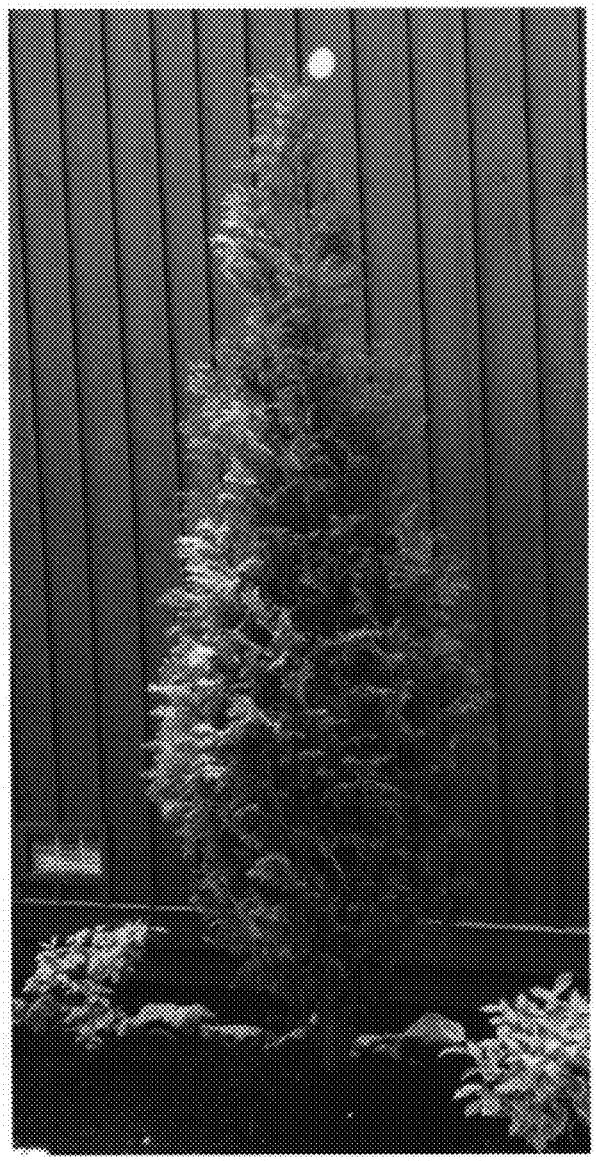
FIG. 1 provides an overall view of the habit of 'Northern Spire'.
Figure 2:
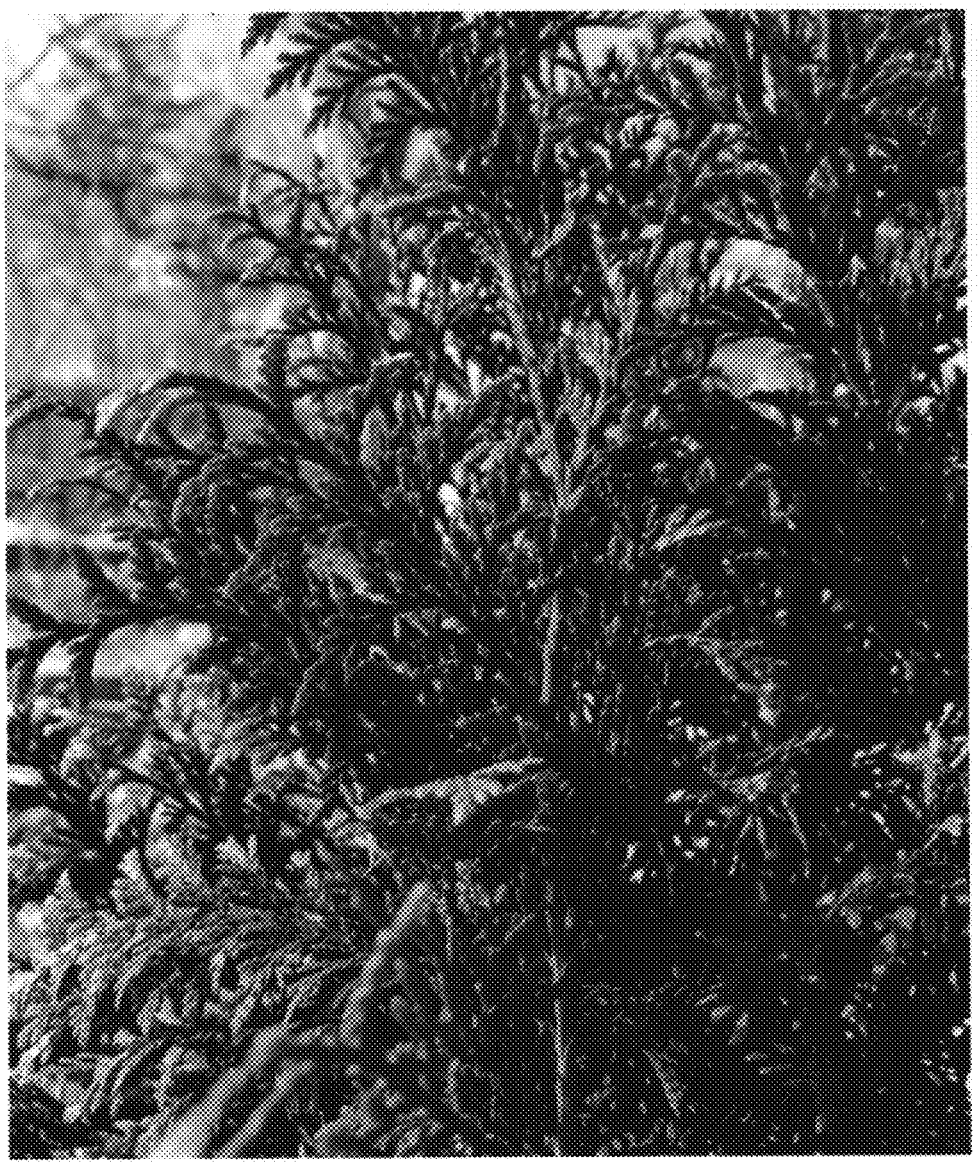
FIG. 2 provides a close-up view of the foliage of 'Northern Spire'.

The colors in the photographs are as close as possible with the photographic and printing technology utilized and the color values cited in the detailed botanical description accurately describe the colors of the new *Thuja.*

DETAILED BOTANICAL DESCRIPTION

The following is a detailed description of the new cultivar as taken from four-year-old plant as grown outdoors in a 3-gallon container in Aldergrove, British Columbia, Wash. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Coniferous, evergreen tree.

*Plant habit.*—Upright and narrowly pyramidal.

*Plant size.*—An average of 4.8 m in height and 91 cm in width as a ten year-old plant in the landscape, 123 cm in height and 60 cm in width on plants four years in age as grown in 3-gallon containers.

*Cold hardiness.*—At least to U.S.D.A. Zone 4.

*Diseases and pests.*—Has shown resistance to Keithia blight caused by *Didymascella thujina* and resistance to deer.

*Root description.*—Fibrous, moderately thick, about 164A in color.

*Propagation.*—Stem cuttings.

*Growth rate.*—Moderately vigorous.

*Root development.*—A rooted cutting is produced in about 4 weeks, a plant 1.2 to 1.5 m in height is produced in about 4 years from a rooted cutting.

Branch description:

*Branch quantity.*—Average of 28 branches from main stem with multiple lateral branches from base (average of 8).

*Branch shape.*—Rounded.

*Branch size.*—Lateral branch average of 30 cm in length and 5 mm in diameter, main stem 3 cm in diameter 2 cm from soil level.

*Branch surface.*—Densely covered with scale-like leaves that are slightly glossy to matte and glabrous, scale-like leaves; whorled in group of 2 to 4 leaves per whorl, 12 per 2 cm section, 5 mm in length, 2 mm in width, sharp acuminate apex, color when young is 143B turning to a blend of 165A and 165B when mature and dry.

*Branching.*—Densely, freely branching, compact.

*Branch arrangement.*—Alternate.

*Branch strength.*—Strong.

*Internode length.*—Average of 1 cm.

*Branch color.*—Young branches; matches surface of scale-like leaf color, mature stems; a blend of 199A, 196A and NN137A, older bark; 197A to N200A.

Foliage description:

*Leaf arrangement.*—Alternate.

*Leaf attachment.*—Sessile.

*Leaf shape.*—Linear, scale-like.

*Leaf division.*—Simple.

*Leaf base.*—Cuneate.

*Leaf apex.*—Short apiculate.

*Leaf venation.*—Not distinguishable, coloration matches leaf coloration.

*Leaf margins.*—Entire.

*Leaf fragrance.*—Slight evergreen fragrance.

*Leaf surface.*—Upper and lower surfaces; glabrous and glossy.

*Leaf color.*—Mature upper surface 143A, lower surface 144B and 141A, immature upper and lower surface 143A, slightly tinged at tips with N144A, fall and winter color; mostly 42B in color.

*Leaf size.*—Up to 12 cm in length and 7 cm in width, average of 9.5 cm in length, 4 cm in width, leaflet average of 2.5 cm in length, 3 mm in width.

*Leaf quantity.*—Average of over 400 leaves per branch, average of 8 to 12 leaflets per leaf.

*Leaf glands.*—Average of 0.3 mm in diameter, rounded in shape, color matches leaf color.

Cone description: Neither male nor female cones have been observed to date.

It is claimed:

1. A new and distinct cultivar of *Thuja* plant named 'Northern Spire' as herein illustrated and described.

* * * * *